US012797168B2

(12) United States Patent
Yue et al.

(10) Patent No.: US 12,797,168 B2
(45) Date of Patent: Nov. 17, 2026

(54) MEDICINAL DENTAL FLOSS CONTAINING GUM CARE ACTIVES

(71) Applicants: Danyang L. Yue, Taiyuan (CN); Li Li, Cincinnati, OH (US)

(72) Inventors: Danyang L. Yue, Cambridge, MA (US); Xin Shu Yue, Cincinnati, OH (US); Li Li, Cincinnati, OH (US); Yingge Yue, Cincinnati, OH (US)

( * ) Notice: Subject to any disclaimer, the term of this patent is extended or adjusted under 35 U.S.C. 154(b) by 115 days.

(21) Appl. No.: 18/684,276

(22) PCT Filed: Sep. 22, 2022

(86) PCT No.: PCT/CN2022/120430

§ 371 (c)(1),
(2) Date: Feb. 16, 2024

(87) PCT Pub. No.: WO2023/045998

PCT Pub. Date: Mar. 30, 2023

(65) Prior Publication Data

US 2025/0025270 A1 Jan. 23, 2025

Related U.S. Application Data

(60) Provisional application No. 63/247,000, filed on Sep. 22, 2021.

(51) Int. Cl.

| | |
|---|---|
| ***A61C 15/04*** | (2006.01) |
| ***A61K 8/21*** | (2006.01) |
| ***A61Q 11/00*** | (2006.01) |

(52) U.S. Cl.

CPC .............. *A61C 15/041* (2013.01); *A61K 8/21* (2013.01); *A61Q 11/00* (2013.01)

(58) Field of Classification Search

CPC .......... A61C 15/041; A61K 8/21; A61K 8/22; A61K 8/24; A61Q 11/00

See application file for complete search history.

(56) References Cited

U.S. PATENT DOCUMENTS

| | | | |
|---|---|---|---|
| 4,911,927 | A | 3/1990 | Hill et al. |
| 5,209,251 | A | 5/1993 | Curtis et al. |
| 5,967,155 | A | 10/1999 | Marcon |
| 10,285,924 | B2 | 5/2019 | Focassio et al. |
| 2007/0254067 | A1 | 11/2007 | Ha |

FOREIGN PATENT DOCUMENTS

| | | | | |
|---|---|---|---|---|
| CN | 1082864 | A | | 3/1994 |
| CN | 101426552 | A | * | 5/2009 |
| CN | 106999413 | A | * | 8/2017 |

* cited by examiner

*Primary Examiner* — Robert A Wax
*Assistant Examiner* — Kimberly Barber
(74) *Attorney, Agent, or Firm* — Jenei LLC

(57) ABSTRACT

A dental floss is provided. The dental floss contains gum care actives for gum disease prevention and treatment without staining or bitter taste.

29 Claims, No Drawings

MEDICINAL DENTAL FLOSS CONTAINING GUM CARE ACTIVES

FIELD OF THE INVENTION

The present application relates to a medicinal dental floss comprising a gum care composition.

BACKGROUND OF THE INVENTION 47.2% of Americans aged 30 and above have some sort of periodontal and the percentage increases to 70% for Americans aged 65 and above. Plaque is something that naturally forms around the teeth, and if it combines with other materials it can turn in calculus (tartar), a hardened product that contributes to periodontal diseases. The calculus then can produce by-products that irritate the gums and show signs of gingivitis.

Gingivitis and periodontitis are both frequently occurring oral diseases. If gingivitis isn't cured, it will worsen to become irreversible periodontitis. Periodontitis can cause gingival recession that causes teeth to fall off. Periodontal diseases are often prevented through regular brushing of the tooth surface and careful flossing in the crevice of the teeth. Since brushing alone leaves a lot of food remnant between one's teeth that directly causes gingivitis, flossing is the most effective method of preventing periodontal diseases. However, flossing alone can only remove plaque without further gum care benefits. Therefore, floss needs to be scientifically viable for preventative and cleaning abilities. By adding additional chemicals or drugs onto floss can make this prevention even more effective. There is currently floss with sodium fluoride applied on the market (sodium fluoride can prevent cavities and strengthen the teeth), but stannous fluoride, although more effective in oral care, is not because applying stannous fluoride to floss often causes a bitter taste and stains the teeth.

Tooth decay and dental diseases can be caused by bacterial action resulting from the formation of plaque around the teeth and/or the entrapment of food particles in interstices between the teeth. Removal of plaque and entrapped food particles reduces the incidence of caries, gingivitis, and mouth odors as well as generally improving oral health.

Flossing alone removes plaque but does not treat gingivitis and periodontal diseases. Method of periodontal disease prevention or treatment is to floss interproximal surfaces of teeth and gingival areas. Patients flossing with medicinal agents-impregnated floss will, in effect, be delivering gum-care agents directly to the interproximal tooth surfaces and, more importantly, to subgingival areas where many periodontal pathogens reside.

A useful medicinal agent is a compound providing a desired oral care result, e.g., anti-caries, anti-tartar, and/or antimicrobial activities. In a preferred embodiment, the medicinal agent is selected from the group comprising chlorohexidine, chlorohexidine derivative, stannous fluoride, sodium fluoride, triclosan, and cetyl pyridinium chloride. Although dental floss has historically, at times, been coated with tooth or gum treating compounds, it has served primarily to treat afflictions of the teeth and periodontal tissues at an inefficient degree and these medicinal agents often have staining or bitter effects and metallic taste. To solve the staining and bitter or metallic taste issues, a whitening agent or anti-staining agent formulated with medicinal agent is applied to the dental floss in a single step. Upon use, the medicinal agent and whitening/anti-staining agent are released into the oral cavity of the user, for the benefit of treatment without staining.

Waxed dental flosses containing medicinal agents are also known in the art, and in addition to providing for the removal of food deposits from the internal spaces between teeth, also provide for the release of medicinal agents that will act within the oral environment. Such medicinal agents may prevent tooth decay, or have anti-tartar, antibiotic, antimicrobial, anti-inflammatory, antioxidant, or antiseptic actions. However, these medicinal agents often cause teeth staining therefore it is rarely seen such medicinal floss on the market. Furthermore, these medicinal agents also have bitter or metallic taste when applied in oral care applications. Therefore, there is a need to develop a medicinal floss which can deliver medicinal benefits without staining or bitter taste when use.

While stannous fluoride is preferred because of its known anti bactericidal activity, other fluoride compounds which have been used and are known to be effective for application to tooth and gingival surfaces may be used. Water soluble waxes may be used, if they are non-toxic and non-irritating to the oral cavity and remain stable under the conditions to which dental floss is normally subjected during manufacture, packaging, storage, and use. In this invention, the floss provides an appropriate amount of fluoride and stannous ions to inhibit the formation of dental cavities and, prevent or treat periodontal disease while whitening or anti-staining agents removes tooth staining which could be caused by stannous ions.

SUMMARY OF THE INVENTION

One or more embodiments provide a medicinal dental floss, comprising:

- a dental floss and coating thereon;
- a binder;
- at least one dental medicinal agent, which is used to prevent tooth decay and/or treat periodontal disease; and/or
- optionally at least one whitening agent or anti-staining agent, which is used to remove or prevent staining caused by the dental medicinal agent; and/or
- optionally at least one taste-pacifying agent, which is used to cover up bitter or metallic taste caused by the dental medicinal agent.

In one or more embodiments, the coating on the medicinal dental floss comprises a gum care composition, the composition comprises the dental floss, the binder, the dental medicinal agent, the whitening agent or anti-staining agent, the taste-pacifying agent, or an optional chelating agent; or the composition consists of the dental floss, the binder, the dental medicinal agent, the whitening agent or anti-staining agent, the taste-pacifying agent, or an optional chelating agent.

In one or more embodiments, the binder is water-soluble wax (such as polyethylene glycol); the dental medicinal agent is an ionic active ingredient selected from the group consisting of fluoride ion source and transitional metal ion source, or percarbonate; the whitening agent or anti-staining agent is percarbonate or polyphosphate; and/or the taste-pacifying agent is saccharin, xylitol, methanol, percarbonate or polyphosphate.

In one or more embodiments, the coating on the medicinal dental floss comprises water-soluble wax; and an ionic active ingredient selected from the group consisting of fluoride ion source and transitional metal ion source; and polyphosphate.

In one or more embodiments, the coating on the medicinal dental floss comprises water-soluble wax; and percarbonate.

In one or more embodiments, the coating on the medicinal dental floss comprises water-soluble wax; and an ionic active ingredient selected from the group consisting of fluoride ion source and transitional metal ion source; and percarbonate; and polyphosphate.

In one or more embodiments, wherein the transitional metal ion source is stannous ion source, zinc ion source, or copper ion source.

In one or more embodiments, wherein the ionic active ingredient is stannous fluoride ($SnF_2$).

In one or more embodiments, wherein the percarbonate is sodium percarbonate or potassium percarbonate.

In one or more embodiments, wherein the polyphosphate is sodium polyphosphate, potassium polyphosphate, ammonium polyphosphate, or cadmium polyphosphate.

In one or more embodiments, wherein the coating on the dental floss comprises a chelating agent, which reacts with metal ions.

In one or more embodiments, wherein the ionic active ingredient has an amount of 3%-12% (such as 3%, 4%, 5%, 6%, 7%, 8%, 9%, 10%, 11%, or 12%) by weight of the coating.

In one or more embodiments, wherein the percarbonate has an amount of 10%- 30% (such as 10%, 11%, 12%, 13%, 14%, 15%, 16%, 17%, 18%, 19%, 20%, 21%, 22%, 23%, 24%, 25%, 26%, 27%, 28%, 29%, or 30%) by weight of the coating.

In one or more embodiments, wherein the polyphosphate has an amount of 8%- 30% (such as 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%) by weight of the coating.

In one or more embodiments, the coating on the medicinal dental floss further comprises plasticizer, which is used to adjust elasticity of floss coating to further improve smoothness, balance softness, and/or active release profile.

In one or more embodiments, the plasticizer is glycerin and/or water.

In one or more embodiments, the coating on the medicinal dental floss further comprises solvent for the dental medicinal agent. In one or more embodiments, the dental medicinal agent is ionic active ingredient. In one or more embodiments, the ionic active ingredient is stannous fluoride ($SnF_2$).

In one or more embodiments, the solvent is water. In one or more embodiments, the solvent for the stannous fluoride ($SnF_2$) is water.

In one or more embodiments, the plasticizer and water have an amount of 1.5-5% (for example, 1.5%, 2%, 3%, 4%, or 5%) by weight of the coating.

In one or more embodiments, the glycerin and water have an amount of 1.5-5% (for example, 1.5%, 2%, 3%, 4%, or 5%) by weight of the coating.

In one or more embodiments, the floss releases the dental medicinal agent into teeth cavity sustainably.

In one or more embodiments, the coating on the medicinal dental floss comprises:

polyethylene glycol, which has an amount of 90%-98% (for example, 90%, 91%, 92%, 93%, 94%, 95%, 96%, 97%, or 98%) by weight of the coating;

glycerin, which has an amount of 0.05%-3.0% (for example, 0.05%, 0.1%, 0.5%, 1%, 2%, or 3%) by weight of the coating;

water, which has an amount of 0.08%-3.0% (for example, 0.08%, 0.1%, 0.5%, 1%, 2%, or 3%) by weight of the coating;

stannous fluoride ($SnF_2$), which has an amount of 0.045%-0.90% (for example, 0.045%, 0.08%, 0.1%, 0.5%, 0.1%, 0.2%, 0.3%, 0.4%, 0.5%, 0.6%, 0.7%, 0.8%, or 0.9%) by weight of the coating, preferably 0.090-0.62%, more preferably 0.20%-0.45% (for example, 0.2%, 0.3%, 0.4%); and the total amount of the glycerin and water is from 1.5%-5% (for example, 1.5%, 2%, 3%, 4%, or 5%), by weight of the coating of the dental floss.

In one or more embodiments, the molecule weight of the polyethylene glycol is from 5,000-20,000 (for example, 5,000, 6,000, 7,000, 8,000, 9,000, 10,000, 11,000, 12,000, 13,000, 14,000, 15,000, 16,000, 17,000, 18,000, 19,000, or 20,000) and/or a mixture thereof; preferably 6,000-15,000 (for example, 6,000, 7,000, 8,000, 9,000, 10,000, 11,000, 12,000, 13,000, 14,000, or 15,000) and/or a mixture thereof; more preferably 7,000-12,000 (for example, 7,000, 8,000, 9,000, 10,000, 11,000, or 12,000) and/or a mixture thereof.

One or more embodiments provide a method for cleaning teeth or preventing and/or treating periodontal diseases, including contacting the teeth of a subject with the dental floss of the present application.

One or more embodiments provide a method for preparing a medicinal dental floss, including the following steps:

(1) impregnating a dental floss with the following substances:

at least one dental medicinal agent, which is used to prevent tooth decay and/or treat periodontal disease; and at least one optional whitening agent or anti-staining agent, which is used to remove or prevent staining caused by the dental medicinal agent; and/or at least one optional taste-pacifying agent, which is used to cover up bitter or metallic taste caused by the dental medicinal agent; and an optional chelating agent, which includes but is not limited to polyphosphate at least one optional plasticizer;

(2) coating the dental floss with a binder.

In one or more embodiments, the binder is water-soluble wax (such as polyethylene glycol); the dental medicinal agent is an ionic active ingredient selected from the group consisting of fluoride ion source and transitional metal ion source, or percarbonate; the whitening agent or anti-staining agent is percarbonate or polyphosphate; and/or the taste-pacifying agent is percarbonate or polyphosphate; optionally the plasticizer is glycerin.

In one or more embodiments, the ionic active ingredient has an amount of 3%-12% (such as 3%, 4%, 5%, 6%, 7%, 8%, 9%, 10%, 11%, or 12%) by weight of the coating, the percarbonate has an amount of 10~30% (such as 10%, 11%, 12%, 13%, 14%, 15%, 16%, 17%, 18%, 19%, 20%, 21%, 22%, 23%, 24%, 25%, 26%, 27%, 28%, 29%, or 30%) by weight of the coating, the polyphosphate has an amount of 8%-30% (such as 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%) by weight of the coating and optionally the plasticizer and water have an amount of 1.5%-5% by weight of the coating.

In one or more embodiments, wherein the ionic active ingredient is stannous fluoride ($SnF_2$).

In one or more embodiments, wherein the percarbonate is sodium percarbonate or potassium percarbonate.

In one or more embodiments, wherein the polyphosphate is sodium polyphosphate, potassium polyphosphate, ammonium polyphosphate, or cadmium polyphosphate.

One or more embodiments provide an anti-staining dental floss coated with a dental medicinal agent, typically a stannous compound and an anti-staining or whitening agent that are fixed by a binder such as wax (for example polyethylene glycol). The medicinal agent is rubbed off by contact with teeth and periodontal tissues, thereby treating areas between the teeth and periodontal tissues. The dental floss of this application allows the patient to receive medicinal care directly for anti-caries benefits and gingivitis and periodontal disease treatment without staining teeth caused by commonly used medicinal agents.

One or more embodiments provide a medicinal dental floss applied with gum care actives, the coating on the dental floss comprising: an ionic active ingredient selected from the group consisting of fluoride ion source and metal ion source; polyphosphate; and/or percarbonate.

One or more embodiments also provide a gum care actives or composition applied on floss, coating on the dental floss comprising metal ions, chelating agents, bleaching agents, taste-pacifying agents, whitening agent, and/or wax.

One or more embodiments provide a $SnF_2$-containing medicinal dental floss, the coating on the dental floss comprising: high molecular weight of PEG, water, glycerin and $SnF_2$, the floss could release $SnF_2$ into teeth cavity sustainably.

One or more embodiments provide a $SnF_2$-containing medicinal dental floss, the coating on the dental floss comprises:

90%-98% (w/w, by weight of the coating, same as below)) high molecule weight PEG (such as polyethylene glycol), glycerin of 0.05%-3.0%, water of 0.08%-3.0%, $SnF_2$ of 0.045%-0.90%, and total amount of glycerin and water is from 1.5%-5%, by weight of the coating of the dental floss.

In one or more embodiments, the high molecule weight of PEG is from 5,000-20,000 and/or a mixture thereof, better from 6,000-15000 and/or a mixture thereof; even better from 7,000-12,000 and/or a mixture thereof.

In one or more embodiments, the $SnF_2$ is from 0.045%-0.90%, better from 0.090-0.62%, even better from 0.20%-0.45%, by weight of the coating of the dental floss.

In one or more embodiments, the total amount of glycerin and water is from 1.5%-5% by weight of the coating of the dental floss.

In one or more embodiments, the effect of floss coating is based on: wearness of the coating to last during the whole mouth flossing; and/or release of $SnF_2$ into oral cavity.

In one or more embodiments, during the flossing process the coating lasts long with least loss helps the smoothness of the flossing, reducing the friction and hurt to the soft gum tissue.

In one or more embodiments, $SnF_2$ needs to be delivered into mouth and release out slowly, it has to be worn out from the floss thread. Once coating wears out the actives should dissolve from matrix in a sustainable way.

In one or more embodiments, glycerin is used here as plasticizer to adjust the elasticity of the coating to further improve smoothness, balance softness, active release profile.

In one or more embodiments, water is used here as both plasticizers and solvent for $SnF_2$. As plasticizer it works alone or together with glycerin from the mechanical properties of floss coating.

DETAILED DESCRIPTION OF THE INVENTION

While the specification concludes with claims particularly pointing out and distinctly claiming the invention, it is believed that the present invention will be better understood from the following description of preferred embodiments.

All percentages used herein are by weight of the overall medicinal dental floss, unless otherwise specified. The ratios used herein are molar ratios of the overall composition, unless otherwise specified. All measurements are made at 25° C., unless otherwise specified.

All publications, patent applications, and issued patents mentioned herein are hereby incorporated in their entirety by reference. Citation of any reference is not an admission regarding any determination as to its availability as prior art to the claimed invention.

Herein, "comprising" means that other steps and other components which do not affect the end result can be added. This term encompasses the terms "consisting of" and "consisting essentially of."

Herein, "effective amount" means an amount of a compound or composition sufficient to significantly induce a positive benefit, preferably an oral health benefit, but low enough to avoid serious side effects, i.e., to provide a reasonable benefit to risk ratio, within the sound judgment of a skilled artisan in the art.

The floss is made of what's commonly used for the manufacturing of floss, such as natural or synthetic fibers of plastic, nylon, and others. The floss' thickness, length, the number of filaments can vary depending on the concentration of gum care actives applied, which can increase or decrease for different effects of treatment. The coating on the floss can also comprise wax (such as polyethylene glycol polymers), or other similar creations that's applied to floss to retain the chemicals.

One or more embodiments refer to coating or impregnating floss with stannous fluoride, and possibly additional chemicals and actives including polyphosphate and sodium percarbonate. Stannous fluoride is the most effective form of fluoride for gum care and gingivitis prevention; however, it has a bitter taste and stains the teeth. Sodium percarbonate is a type of bleaching agent and has stain removal abilities while bettering the taste of stannous fluoride. Sodium percarbonate also is a bleaching agent and has whitening abilities.

One or more embodiments are focused on floss that treats gingivitis and periodontal diseases by utilizing medicinal effects of stannous fluoride and eliminating side effects such as staining teeth and bitter taste from stannous. The reason for this application is to create gingivitis-preventing floss that doesn't have bitter taste or further stains our teeth. Such a floss can drastically prevent and treat periodontal diseases to reduce the number of people troubled with periodontal diseases.

In one or more embodiments, stannous fluoride, sodium percarbonate, or polyphosphate (salts formed from tetrahedral $PO_4$) are applied onto floss with natural wax. The reason to use wax is that chelating agents or bleaching agents are unstable in aqueous solutions; therefore, it's difficult to apply it directly to stannous fluoride floss. Liquid wax allows us to combine stannous fluoride and chelating/bleaching agents by combining them with melted wax, then applying it to floss. A medicinal agent stable in aqueous solutions can also first be coated onto the floss in an aqueous solution, for example stannous fluoride. However, medicinal agents unstable in aqueous solutions, such as the chelating and bleaching agents we previously mentioned, will be combined with melted wax.

Chelating agents are chemical compounds that react with metal ions which improve the metal's stability and make it easier to bond with other substances. Bleaching agents are agents that whiten or lighten another material by oxidizing or reducing the impurities of that material. Metal ions such as stannous, copper and zinc ions are known to be effective anti-microbial agents. Stannous salts include stannous fluoride and stannous chloride (U.S. Pat. No. 5,004,597). Other suitable stannous salts include stannous acetate, stannous tartrate, and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate (U.S. Pat. No. 4,022, 880). Examples of suitable copper ion sources are listed in U.S. Pat. No. 5,534,243. These metal ions provide anti-gingivitis and plaque prevention benefits and may also improve breath and reduce sensitivity. However, metal ions are also known to be astringent in taste. Stannous and copper are also known to cause staining on the tooth surfaces. Therefore, other materials are needed to offset the effects of these metal ions.

In one or more embodiments, sodium percarbonate is a bleaching agent because it has whitening abilities. Polyphosphate is a chelating agent that has low toxicity and combines metals in oral care products, which allows it to bond with the Ca (Calcium) ions of teeth and helps with additional gingival care. Certain polyphosphates that function as anti-tartar agents are known to be unstable in high aqueous systems and to react with ionic fluoride in oral gum care compositions at ambient temperature. There are also optional agents to be used in place of or in combination with the polyphosphate include materials that effectively reduce calcium phosphate mineral deposition related to calculus formation. Agents included are pyrophosphates, tripolyphosphates, synthetic anionic polymers, including polyacrylates and copolymers of maleic anhydride or acid and methyl vinyl ether, as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof (U.S. Pat. No. 4,627,977 to Gaffar).

Stannous fluoride prevents cavities and gum diseases, sodium percarbonate improves whitening and gum care, and polyphosphate is also anti-stain and prevents tartar creation. Furthermore, polyphosphate and sodium percarbonate have other ingredients commonly used in floss that can offset the bitter stannous taste while polyphosphate offers stain removal and whitening effects. Therefore, stannous fluoride can be combined with either sodium percarbonate or polyphosphate to provide gum care and whitening effects in floss. At the same time, sodium percarbonate can also be used alone to prevent gingivitis and remove stains on teeth. Transitional metal compounds, specifically stannous fluoride, can be combined with chelating and bleaching agents such as sodium percarbonate and polyphosphate.

The gum care composition in the medicinal dental floss comprises main or essential components as well as other or optional components. The main or essential and other or optional components of the medicinal dental floss are described in the following paragraphs.

Main Components

Ionic Active Ingredient

The gum care actives applied on floss of the present invention preferably comprise an effective amount of an ionic active ingredient selected from the group consisting of a fluoride ion source, a stannous ion source, a zinc ion source, a copper ion source, and mixtures thereof.

A. Fluoride Ion Source

The fluoride ion source herein is a soluble fluoride source capable of providing free fluoride ions. Soluble fluoride ion sources include sodium fluoride, stannous fluoride, indium fluoride, zinc fluoride, and sodium monofluorophosphate. Sodium fluoride and stannous fluoride are the preferred soluble fluoride ion sources. As noted above, previous disclosures of comprising a polyphosphate having a chain length of about 4 or more have indicated that sodium monofluorophosphate is the preferred fluoride ion source. This is because sodium monofluorophosphate has been found to be more stable than other fluoride sources in the presence of a polyphosphate having an average chain length of about 4 or more, as well as in compositions containing a relatively higher level of water. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The fluoride ion source in the present gum care compositions can present as a solid dispersion in the composition during storage, prior to actual flossing usage of the composition by a consumer. The level of water in the present compositions is too low to permit the fluoride source to dissolve in the composition during storage. Thus, there is no obvious interaction between the fluoride ion and the polyphosphate during storage, providing a stable composition during storage. When the composition is contacted by saliva and/or water at the time of flossing, the fluoride source will be dispersed, and the active ion will be delivered to the oral cavity.

The fluoride ion source in the present gum care compositions can also present as a liquid dispersion that's soaked onto the floss. Polyphosphate would be integrated with melted wax and then applied onto the floss so there is no obvious interaction between the fluoride ion and polyphosphate or during storage, providing a stable composition during storage. When the composition is contacted by saliva and/or water at the time of flossing, the fluoride source will be released, and the active ion will be delivered to the oral cavity.

The present gum care compositions in the medicinal dental floss may contain a soluble fluoride ion source capable of providing from about 50 ppm to about 3500 ppm, and preferably from about 500 ppm to about 3000 ppm of free fluoride ions. To deliver the desired amount of fluoride ions, fluoride ion source may be present in the total composition at an amount of from about 0.1% to about 5%, preferably from about 0.2% to about 1%, and more preferably from about 0.3 to about 0.6%, by weight of the total composition.

B. Metal Ion Source

The present invention may comprise a metal ion source that provides stannous ions, zinc ions, copper ions, or mixtures thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions have been found to help in the reduction of gingivitis, plaque, sensitivity, and improved breath benefits. The efficacy of these metal ions in the present compositions is not reduced by the polyphosphate.

Stannous, zinc and copper ions are derived from the metal ion source(s) found in the gum care composition in an effective amount. An effective amount is defined as from at least about 1000 ppm metal ion, preferably about 2,000 ppm to about 15,000 ppm. More preferably, metal ions are present in an amount from about 3,000 ppm to about 13,000 ppm and even more preferably from about 4,000 ppm to about 10,000 ppm. This is the total amount of metal ions (stannous, zinc, copper and mixtures thereof) that is present in the compositions for delivery to the tooth surface.

Oral care products containing stannous salts, particularly stannous fluoride and stannous chloride, are described in U.S. Pat. No. 5,004,597 to Majeti et al. Other descriptions of stannous salt are found in U.S. Pat. No. 5,578,293. The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880. Examples of suitable copper ion sources are listed in U.S. Pat. No. 5,534,243.

The combined metal ion source(s) will be present in an amount of from about 3% to about 12%, by weight of the coating of the final medicinal dental floss. Preferably, the metal ion sources are present in an amount of from about 4 to about 7%.

Whitening Agents

The medicinal dental floss may also make use of one or more peroxide-based compounds as whitening agents such as, but not limited to, calcium peroxide, and percarbonate (sodium percarbonate and/or potassium percarbonate). Their use will help remove dental plaques and whiten teeth and so thereby reduce the incidence of dental caries and other related diseases. This ability to reduce dental decay stems from the fact that oxygen is released during their decompositions. Thus, when a peroxide-based compound is utilized in the mouth, the decomposed release of oxygen will vigorously attack all oral bacteria and plaques and help whitening teeth.

Peroxide-based compounds (solid form is preferred to preserve peroxide stability) being mostly alkaline in nature will also facilitate the neutralization of oral acids. The level of alkalinity is not set at any specific figure or amount and thus can be suitably adapted to the medicinal dental floss desired. The concentration of the peroxide-based compound will also vary to some extent upon the type of peroxide compound employed and the final formulations used in the medicinal dental floss. As a result, the amount employed is given extensive leeway in both use and concentration but both the quantity as well as the level of alkalinity must be of a safe level.

Peroxide Source

The present invention may include a peroxide source in the gum care composition. The peroxide source is selected from the group consisting of calcium peroxide, urea peroxide, and mixtures thereof. The preferred peroxide source is calcium peroxide. The following amounts represent the amount of peroxide raw material, although the peroxide source may contain ingredients other than the peroxide raw material.

Polyphosphate Source

The present application includes a polyphosphate source. Polyphosphates are known to help retard calculus formation. However, it is also known that polyphosphates with an average chain length greater than about 4 will also react with ionic fluoride in oral gum care compositions at ambient temperature and produce monofluorophosphate ions, in addition to altering the pH of the composition. This reaction compromises the efficacy of the oral composition and its ability to provide stable ionic fluoride and polyphosphate to the oral surfaces. It is also known that to have stable polyphosphate, the total water content and pH of the composition must be controlled to reduce the hydrolysis of the polyphosphate.

A polyphosphate is generally understood to consist of two or more phosphate molecules arranged primarily in a linear configuration, although some cyclic derivatives may be present. Although pyrophosphates are a polyphosphate, the polyphosphates desired are those having around four or more phosphate molecules. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 6 to about 125, more preferred from about 11 to about 50. Preferred are polyphosphates manufactured by FMC Corporation which are commercially known as Sodaphos (n≈6), Hexaphos (n≈13), and Glass H (n≈21). These polyphosphates may be used alone or in a combination thereof.

The phosphate sources are described in more detail in Kirk & Othmer, Encyclopedia of Chemical Technology, Fourth Edition, Volume 18, Wiley-Interscience Publishers (1996). An effective amount of a polyphosphate source will typically be from about 0.1% to about 30%, preferably from about 1% to about 26%, more preferably from about 4% to about 20%, and most preferably from about 5% to about 13%, by weight of the coating of the medicinal dental floss.

Water-Soluble Wax

Floss is usually covered in water-soluble wax, which includes polyethylene glycol, petroleum wax (melting point range is: 38° to 54° C.), beeswax (melting point range is: 60° C. to 62° C.), microcrystalline wax (melting point range is: 63° C. to 93° C.), Coconut oil (melting point: 24° C., often used with microcrystalline wax).

U.S. Pat. No. 2,598,724 discloses methods of increasing the melting point of petrolatum wax which comprises subjecting ethylene and a petrolatum to the action of an organic peroxide condensation catalyst at a temperature at least as high as the decomposition temperature of said catalyst.

Other Components

Anti-Calculus Agents

Optional agents to be used in place of or in combination with the polyphosphate include such materials known to be effective in reducing calcium phosphate mineral deposition related to calculus formation. Agents included are pyrophosphates, tripolyphosphates, synthetic anionic polymers [including polyacrylates and copolymers of maleic anhydride or acid and methyl vinyl ether (e.g., Gantrez), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Polishing or Abrading Agents

An abrasive polishing agent may also be included in the medicinal dental floss. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be, used. If the composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, "Zeodent", particularly the silica carrying the designation "Zeodent 119." The types of silica dental abrasives useful in the floss of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. The abrasive in the medicinal dental floss described herein is generally present at a level of from about 6% to about 70% by weight of the coating. Preferably, floss contain from about 10% to about 50% (such as 10%, 20%, 30%, 40% or 50%) of abrasive by weight of the coating.

One or more polishing or abrading agents may also be utilized in the medicinal dental floss. The type of abrading agents employed is not restricted to any specific types or quantities. This effectively allows the abrading compounds used to suit the final effects desired. In any case, their incorporation will help clean and polish teeth and so help produce a smooth and shiny dental surface that will resist discoloration, bacterial accumulation, and retention. Reducing plaques will also reduce the number of oral acids and, in turn, dental demineralization. Moreover, as dental surfaces become cleaner the medicinal performances of other ingredients such fluorides or periodontal treatment agents such as stannous ions will notably increase. Examples of polishing or abrading agents may include a boride, carbide, carbonate, bicarbonate, nitride, oxide, dioxide, phosphate, silicate or sulfide of such elements as aluminum, calcium, iron, magnesium, potassium, silicon, sodium, tin, titanium, tungsten, zinc, zirconium, and any mixtures thereof. Other compounds and mixtures are, of course, available.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present medicinal dental floss may contain from about 10% to about 30%, preferably from about 5% to about 30%, and most preferably from about 5% to about 18% of an alkali metal bicarbonate salt by weight of the coating.

Coloring agents may also be added to the present gum care composition in the medicinal dental floss. Coloring agents generally comprise from about 0.01% to about 1% by weight of the coating.

A flavor system can also be added to the compositions in the medicinal dental floss. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present medicinal dental floss are the paramenthan carboxyamide agents such as N-ethyl-p-menthan-3-carboxamide (known commercially as "WS-3") and mixtures thereof. A flavor system is generally used in the medicinal dental floss at levels of from about 0.001% to about 0.1% by weight of the coating Sweetening agents can be added to the compositions in the medicinal dental floss. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in floss at levels of from about 0.005% to about 0.01% by weight of the coating.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The antimicrobials include quaternary ammonium salts and bis-biquanide salts, among others. Triclosan monophosphate is a preferred additional antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are examplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey. Other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan is a preferred antimicrobial agent for inclusion in the present compositions. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. The antimicrobial agents and enzymes may be present in either the first or second compositions. The quaternary ammonium agents, stannous salts, and substituted guanidines are preferably present in the second composition. These agents may be present at levels of from about 0.01% to about 1.5% by weight of the coating.

An herbal agent, including but not limited to, golden thread extract, honeysuckle extract, and mixtures thereof, may also be present in the medicinal dental floss herein at levels of from about 0.01% to about 0.05%. Such herbal agents are believed to provide anti-bacterial efficacy. Polyphenols may further be included at levels from about 0.01% to about 2%. A preferred polyphenol is tea polyphenol.

An effective amount of a desensitizing agent may also be incorporated into the present medicinal dental floss. The desensitizing agents include those selected from alkaline metal salts with a chloride, nitrate sulfate, or acetate of a group II metal or aluminum or polymerizable monomer to occlude the tubules, alkaline metal or ammonium nitrate, ammonium oxylate, citric acid and sodium citrate. Preferred salts are potassium nitrate, potassium citrate, and mixtures thereof. Such desensitizing agents are disclosed in e.g., U.S. Pat. No. 5,718,885.

For compositions in the medicinal dental floss that contain stannous, a stain reducing agent such as Plasdone S-630 or aluminum hydrate may further be added to the composition. Plasdone is polyvinyl pyrrolidone (PVP) that can be synthesized by polymerizing vinylpyrrolidone. Commercially, it has been produced as a series of products having mean molecular weights ranging from 10,000 to 700,000. Herein, the low molecular weights and middle molecular weights (from about 10,000 to about 100,000) are preferred. In order to remove stain effectively, the level of PVP is preferably from about 0.2% to about 3% and more preferably from about 1.0% to about 2.0%.

Methods of Manufacturing

A method of making an improved dental floss having medicinal properties with whitening or anti-staining effects comprising forming a mixture of dry medicinal powder and whitening/anti-staining powder consisting of an ionic medicinal ingredient selected from the group consisting of fluoride ion source and transition metal ion source; polyphosphate; and/or sodium percarbonate, impregnating floss with said mixture and subsequently coating the floss with a pre-melted water-soluble wax to trap the medicinal and whitening or anti-staining agents on floss thereon. (PEG needs to pre-melt before application)

Another method of making an improved dental floss is having desired amount of medicinal agents such as stannous fluoride dissolved into water with or without glycerin, add the $SnF_2$ solution into pre-melt polyethylene glycol (PEG) wax to mix homogenously, then soak the floss into the PEG wax, then cool down to dry the floss to yield stannous fluoride enriched floss.

Usage

In operative use, the floss of the present application is inserted into the crevices or spaces between the mouth teeth and then is pulled there through. Thus, the medicinal, whitening, and anti-staining agents are wiped off the floss and onto the dental crevice surfaces and periodontal tissues thereby treating the same and inhibiting germ growth there and the like, while preventing staining and minimizing metallic bitter taste.

An effective delivery of fluoride to a person's teeth is about 0.32 mg per 100 cm of floss. It is seen that a stannous fluoride together with wax, such as polyethylene glycol wax, will effectively deliver fluoride to a person's teeth and Sn ion to periodontal tissues.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Medicinal agents added to wax have been found to be problematic due to inefficient release from the insoluble wax. Thus, water-soluble waxes such as polyethylene glycol derivative waxes were used in the examples.

Example 1-1

Formulation: Stannous Fluoride ($SnF_2$)+Sodium Percarbonate+Wax

Solid stannous fluoride fine powder was dissolved in water to make a stannous fluoride solution, then soaked the floss into the solution, then dried the floss to yield 4000 ppm of F content on the stannous fluoride enriched floss. And then fine powder of sodium percarbonate (10~30% by weight of the coating on the finished medicinal floss) was added to melted water-soluble polyethylene glycol wax for homogeneous mixing. The mixture was used to coat sections of multi-filament unwaxed and stannous enriched dental floss, using apparatus designed for that purpose. After allowing the percarbonate-intergraded wax to solidify on the stannous enriched floss, the floss was cut into predetermined sections. The preparation of the $SnF_2$/sodium percarbonate coated waxed floss as completed under aerobic conditions.

Example 1-2

Formulation: Stannous Fluoride ($SnF_2$)+Sodium Percarbonate+Wax

Solid stannous fluoride fine powder was measured to yield 4000 ppm F content, and fine powder of sodium percarbonate (10~30% by weight of the coating on finished medicinal floss) was added to melted water-soluble polyethylene glycol wax for homogeneous mixing. The final mixture was used to coat sections of multi-filament unwaxed dental floss, using apparatus designed for that purpose. After allowing the $SnF_2$/sodium percarbonate wax formulation to solidify on the floss, the floss was cut into predetermined sections.

The preparation of the $SnF_2$/sodium percarbonate coated waxed floss as completed under aerobic conditions.

Example 2

Formulation: Stannous Fluoride ($SnF_2$)+Sodium Polyphosphate+Wax

The floss was produced having loadings of stannous fluoride of 10.7% by weight, 7.5% by weight and 3.75% by weight, all have 10% by weight sodium polyphosphate. The floss had a nominal thickness of 0.07 mm and a width of 2.6 mm. The floss was cut into lengths of 100 cm and placed in 10 ml of distilled water at about 26° C. for 10 minutes. The floss was then removed and the water was analyzed for ionic fluoride. The amount of ionic fluoride that is leached from each sample was given in Table 1.

TABLE 1

| Floss Length | Floss $SnF_2$ % | F Content of HOH |
|---|---|---|
| 100 cm | 10.7 | 24.6 mg |
| 100 cm | 7.5 | 9.3 mg |
| 100 cm | 3.75 | 7.8 mg |

Example 3

Formulation: Stannous Fluoride ($SnF_2$)+Potassium Percarbonate (Gum Care, No Stain)+Wax The floss was applied with $SnF_2$, potassium percarbonate, and wax by similar method as that in Example 1-1 or Example 1-2 and analyzed by the similar method as that in Example 2.

Stannous fluoride (transitional metal) and potassium percarbonate (bleaching agent) achieved gingival care. Since stannous fluoride resulted in staining, potassium percarbonate can offset the staining with its bleaching effects. This combination was applied to floss through wax.

Example 4

Formulation: Stannous Fluoride ($SnF_2$)+Potassium Polyphosphate (Gum Care, No Stain)+Wax The floss was applied with $SnF_2$, potassium polyphosphate, and wax by similar method as that in Example 1-1 or Example 1-2 and analyzed by the similar method as that in Example 2.

Stannous fluoride (transitional metal) and potassium polyphosphate (chelating and bleaching agent) achieved gingival care from both the stannous fluoride and potassium polyphosphate. At the same time, potassium polyphosphate reduced calcium phosphate formation and removed stains on teeth. This combination was applied to floss through wax.

Example 5

Formulation: Sodium Percarbonate (Gum Care, No Stain, and Whitening)+Wax

The floss was applied with sodium percarbonate and wax by similar method as that in Example 1-1 or EXAMPLE 1-2 and analyzed by the similar method as that in Example 2.

Sodium percarbonate alone had gum care effects while removing stains and whitening the teeth. This combination was applied to floss through wax.

Example 6

Formulation: Stannous Fluoride ($SnF_2$)+Sodium Polyphosphate (Gum Care, No Stain)+Sodium Percarbonate (Gum Care, Whitening)+Wax The floss was applied with $SnF_2$, sodium polyphosphate, sodium percarbonate, and wax by similar method as that in Example 1-1 or Example 1-2 and analyzed by the similar method as that in Example 2.

Stannous fluoride (transitional metal) and sodium polyphosphate (chelating and bleaching agent) achieved gingival care from both the stannous fluoride and sodium polyphosphate. At the same time, sodium polyphosphate reduced calcium phosphate formation and removed stains on teeth. This combination was applied to floss through wax.

Example 7

Formulation:

stannous fluoride ($SnF_2$)+PEG (polyethylene glycol)+glycerin+water+blue dye (not part of the formulation, dye used here as a marker to check the durability and leftover in oral cavities)

Making Process:

PEG was melted at 90° C. $SnF_2$ and blue dye was dissolved in water and then mixed with glycerin. The mixture was added into the melted PEG. The floss was coated with melted PEG under agitation.

Materials:

Different molecular weights of Polyethylene glycol PEG4000, 8000, 10000, 14000, 18000: Clariant, Food Grade;

Glycerin: Wilmar International, food grade, purity 99.5%;

$SnF_2$: Honeywell, pharm grade, purity 99%;

Blue Dye: No 5, food grade, Clariant;

Instruments:

Soluble fluoride testing: Mettler Toledo Fluoride Meter;

Coffee bean miller, Philipps;

Mouth model with 32 teeth: PRO2001-UL-SP-FEM-32, Nissin.

Methods:

Soluble Fluoride Testing

A water bath was set up at 37° C. (+/−1° C.), then 180.0 g DI water was added into a glass baker. Agitation was started at 30 rpm. 20.0 g of stannous fluoride containing PEG material was added into a coffee bean miller to mill for 3 min. Until the temperature reached 37° C., the small stannous fluoride containing PEG particles from the coffee bean mixer was transferred totally to the baker and started the timer to read the soluble fluoride at preset time points.

Durability Test 25 cm coated floss preblended with blue dye was taken. DI water was sprayed onto the teeth model. Then the whole mouth was flossed to test both easiness of flossing and residue of coating materials in oral cavities. The data is shown in the table below.

| Composition A | | Composition B | | Composition C | | Composition D | |
|---|---|---|---|---|---|---|---|
| PEG4000 | 97.00%** | PEG8000 | 97.00% | PEG8000 | 97.00% | PEG8000 | 97.00% |
| SnF2 | 0.45% | SnF2 | 0.45% | SnF2 | 0.45% | SnF2 | 0.45% |
| Water | 1.55% | Water | 1.55% | Water | 1.55% | Water | 1.55% |
| blue dye (durability indicator) | 5 ppm | blue dye | 5 ppm | blue dye | 5 ppm | blue dye | 5 ppm |
| Glycerin | 1.00% | Glycerin | 1.00% | Glycerin | 3.00% | Glycerin | 6.00% |
| Mechanical properties | | | | | | | |
| Softness at room temp | soft, easy to deform | | elastic, not deformable | | elastic, not deformable | | elastic and deformable |
| Durability | easy to wear out | | some wear out, an even blue layer on thread | | with increase wear out but an even blue layer on thread | | easy to wear out |
| Fluoride Availability* | 28, 48, 95 | | 20, 45, 86 | | 25, 53, 90 | | 32, 68, 100 |

| Composition A | Composition E | | Composition F | | Composition G | |
|---|---|---|---|---|---|---|
| PEG4000 | PEG10000 | 96.00% | PEG14000 | 95.00% | PEG18000 | 92.00% |
| SnF2 | SnF2 | 0.45% | SnF2 | 0.45% | SnF2 | 0.45% |
| Water | Water | 1.55% | Water | 1.55% | Water | 1.55% |
| blue dye (durability indicator) | blue dye | 5 ppm | blue dye | 5 ppm | blue dye | 5 ppm |
| Glycerin | Glycerin | 2.00% | Glycerin | 3.00% | Glycerin | 6.00% |
| Mechanical properties | | | | | | |
| Softness at room temp | | Elastic, but not deformable | | rigid, not deformable | | very rigid, not deformable |
| Durability | | some wear out, an even blue layer on thread | | some wear out, even blue layer on thread | | some wear out, broken blue layer on thread |
| Fluoride Availability* | | 18, 48, 80 | | 12, 25, 37 | | 8, 15, 35 |

*Time point to check out soluble fluoride: 5, 15, 30 min in under 37 degC. DI water under agitation at 30 rpm. 1:9 of PEG wax: DI water is used to simulate flossing in ˙eal mouth m agitation. In theory total soluble fluoride is 109 ppm. Success criteria is defined as no less than 60% (65 ppm) of total available fluoride dissolved at 30 min

**"%" means by weight of the coating on the medicinal dental floss

It is understood that the examples and embodiments described herein are for illustrative purposes only and that various modifications or changes in light thereof will be suggested to one skilled in the art without departing from the scope of the present invention.

What is claimed is:

1. A medicinal dental floss, comprising:

a dental floss; and a coating disposed on the dental floss, the coating comprising:

polyethylene glycol in an amount of 90% to 98% by weight of the coating;

glycerin in an amount of 0.05% to 3.0% by weight of the coating;

water in an amount of 0.08% to 3.0% by weight of the coating; and stannous fluoride in an amount of 0.045% to 0.90% by weight of the coating;

wherein a total amount of the glycerin and the water is from 1.5% to 5% by weight of the coating.

2. The medicinal dental floss of claim 1, wherein the polyethylene glycol has a molecular weight of from 5,000 to 20,000.

3. The medicinal dental floss of claim 1, the coating comprising:

wherein the polyethylene glycol has a molecular weight of from 6,000 to 15,000.

4. The medicinal dental floss of claim 1, wherein the polyethylene glycol has a molecular weight of from 7,000 to 12,000.

5. The medicinal dental floss of claim 1, wherein the stannous fluoride is present in an amount of from 0.090% to 0.62% by weight of the coating.

6. The medicinal dental floss of claim 1, wherein the stannous fluoride is present in an amount of from 0.20% to 0.45% by weight of the coating.

7. The medicinal dental floss of claim 1, wherein the coating further comprises a chelating agent.

8. The medicinal dental floss of claim 1, wherein the coating further comprises a polyphosphate.

9. The medicinal dental floss of claim 8, wherein the polyphosphate is sodium polyphosphate, potassium polyphosphate, or ammonium polyphosphate.

10. The medicinal dental floss of claim 8, wherein the coating further comprises a chelating agent.

11. The medicinal dental floss of claim 1, wherein the coating further comprises a percarbonate.

12. The medicinal dental floss of claim 11, wherein the percarbonate is sodium percarbonate or potassium percarbonate.

13. The medicinal dental floss of claim 11, wherein the coating further comprises a polyphosphate.

14. The medicinal dental floss of claim 1, wherein the coating further comprises a taste-pacifying agent.

15. The medicinal dental floss of claim 14, wherein the taste-pacifying agent is saccharin, xylitol, menthol, percarbonate, or polyphosphate.

16. The medicinal dental floss of claim 1, wherein the glycerin functions as a plasticizer in the coating.

17. The medicinal dental floss of claim 1, wherein the water functions as a solvent for the stannous fluoride.

18. The medicinal dental floss of claim 1, wherein the coating is configured to release stannous fluoride during use of the medicinal dental floss.

19. The medicinal dental floss of claim 1, wherein the glycerin functions as a plasticizer in the coating and the water functions as a solvent for the stannous fluoride.

20. The medicinal dental floss of claim 11, wherein the coating further comprises a chelating agent.

21. The medicinal dental floss of claim 2, wherein the stannous fluoride is present in an amount of from 0.090% to 0.62% by weight of the coating.

22. The medicinal dental floss of claim 21, wherein the polyethylene glycol has a molecular weight of from 5,000 to 20,000.

23. The medicinal dental floss of claim 22, wherein the stannous fluoride is present in an amount of from 0.20% to 0.45% by weight of the coating.

24. A method for cleaning teeth or treating periodontal disease, comprising contacting the teeth and gingival areas of a subject with the medicinal dental floss of claim 1.

25. A method for preparing a medicinal dental floss, comprising coating a dental floss with a coating composition comprising:
polyethylene glycol in an amount of 90% to 98% by weight of the coating composition;
glycerin in an amount of 0.05% to 3.0% by weight of the coating composition;
water in an amount of 0.08% to 3.0% by weight of the coating composition; and
stannous fluoride in an amount of 0.045% to 0.90% by weight of the coating composition;
wherein a total amount of the glycerin and the water is from 1.5% to 5% by weight of the coating composition.

26. The method of claim 25, wherein
the polyethylene glycol has a molecular weight of from 5,000 to 20,000.

27. The method of claim 25, wherein the stannous fluoride is present in an amount of from 0.090% to 0.62% by weight of the coating composition.

28. The method of claim 25, wherein the coating composition further comprises a polyphosphate.

29. The method of claim 25, wherein the coating composition further comprises a percarbonate.

* * * * *